(12) United States Patent
Suchalkin et al.

(10) Patent No.: US 9,590,140 B2
(45) Date of Patent: Mar. 7, 2017

(54) BI-DIRECTIONAL DUAL-COLOR LIGHT EMITTING DEVICE AND SYSTEMS FOR USE THEREOF

(71) Applicants: Sergey Suchalkin, Stony Brook, NY (US); Gregory Belenky, Port Jefferson, NY (US); Leon Shterengas, Port Jefferson, NY (US); David Westerfeld, Central Islip, NY (US)

(72) Inventors: Sergey Suchalkin, Stony Brook, NY (US); Gregory Belenky, Port Jefferson, NY (US); Leon Shterengas, Port Jefferson, NY (US); David Westerfeld, Central Islip, NY (US)

( * ) Notice: Subject to any disclaimer, the term of this patent is extended or adjusted under 35 U.S.C. 154(b) by 0 days.

(21) Appl. No.: 14/789,438

(22) Filed: Jul. 1, 2015

(65) Prior Publication Data
US 2016/0005921 A1    Jan. 7, 2016

Related U.S. Application Data

(60) Provisional application No. 62/020,580, filed on Jul. 3, 2014.

(51) Int. Cl.
*H01L 33/08* (2010.01)
*H01L 33/06* (2010.01)
(Continued)

(52) U.S. Cl.
CPC .......... *H01L 33/08* (2013.01); *G01N 21/314* (2013.01); *G01N 21/3504* (2013.01);
(Continued)

(58) Field of Classification Search
CPC ................. H01L 33/08; G01N 2021/3181
See application file for complete search history.

(56) References Cited

U.S. PATENT DOCUMENTS

| | | | | |
|---|---|---|---|---|
| 4,773,074 A | * | 9/1988 | Hunsperger | ....... G02B 6/12004 257/E31.096 |
| 4,948,960 A | * | 8/1990 | Simms | ................. G02B 6/4202 250/227.11 |

(Continued)

OTHER PUBLICATIONS

Grundmann, M. "Multi-color light emitting diode using polarization-induced tunnel junctions" phys. stat. sol. vol. 4, No. 7 pp. 2830-2833 published online May 31, 2007.*

(Continued)

*Primary Examiner* — Matthew Landau
*Assistant Examiner* — Grant Withers
(74) *Attorney, Agent, or Firm* — Alexey Kudymov

(57) ABSTRACT

An LED optimized for use in low-cost gas or other non-solid substance detection systems, emitting two wavelengths ("colors") of electromagnetic radiation from the same aperture is disclosed. The LED device emits a light with a wavelength centered on an absorption line of the target detection non-solid substance, and also emits a reference line with a wavelength that is not absorbed by a target non-solid substance, while both wavelengths are transmitted through the atmosphere with low loss. Since the absorption and reference wavelengths are emitted from the same exact aperture, both wavelengths can share the same optical path, reducing the size and cost of the detector while also reducing potential sources of error due to optical path variation.

14 Claims, 9 Drawing Sheets

(51) Int. Cl.
   *H01L 33/00* (2010.01)
   *H01L 33/30* (2010.01)
   *G01N 21/3504* (2014.01)
   *G01N 21/31* (2006.01)

(52) U.S. Cl.
   CPC .......... *H01L 33/0025* (2013.01); *H01L 33/06* (2013.01); *H01L 33/30* (2013.01); *G01N 2021/3181* (2013.01)

(56) References Cited

U.S. PATENT DOCUMENTS

| | | | | |
|---|---|---|---|---|
| 5,097,299 | A * | 3/1992 | Donhowe | G02B 6/4246 257/13 |
| 5,548,137 | A * | 8/1996 | Fan | B82Y 20/00 257/101 |
| 5,910,851 | A * | 6/1999 | Flaherty | H04B 10/40 398/110 |
| 6,163,038 | A * | 12/2000 | Chen | H01L 33/32 257/101 |
| 7,323,721 | B2 * | 1/2008 | Liao | B82Y 20/00 257/90 |
| 7,875,478 | B2 * | 1/2011 | Yeh | B82Y 20/00 257/103 |
| 2003/0006430 | A1 * | 1/2003 | Shibata | H01L 33/08 257/200 |
| 2004/0061115 | A1 * | 4/2004 | Kozawa | H01L 33/08 257/79 |
| 2010/0224857 | A1 * | 9/2010 | Soh | H01L 27/153 257/13 |
| 2011/0180781 | A1 * | 7/2011 | Raring | H01L 27/156 257/13 |
| 2011/0266520 | A1 * | 11/2011 | Shur | H01L 33/06 257/13 |
| 2011/0284824 | A1 * | 11/2011 | Liu | H01L 33/04 257/13 |
| 2012/0120972 | A1 * | 5/2012 | Belenky | B82Y 20/00 372/20 |
| 2012/0126201 | A1 * | 5/2012 | Liu | H01L 21/0237 257/13 |
| 2012/0248407 | A1 * | 10/2012 | Toyoda | H01L 33/06 257/13 |
| 2013/0270514 | A1 * | 10/2013 | Saxler | H01L 33/08 257/13 |
| 2013/0285076 | A1 * | 10/2013 | Liu | H01L 33/08 257/88 |
| 2013/0320308 | A1 * | 12/2013 | Lee | H01L 51/52 257/40 |
| 2014/0001435 | A1 * | 1/2014 | Witanachchi | H01L 33/08 257/13 |
| 2014/0361247 | A1 * | 12/2014 | Choi | H01L 33/06 257/13 |
| 2015/0060904 | A1 * | 3/2015 | Robin | H01L 33/005 257/89 |
| 2015/0318448 | A1 * | 11/2015 | Nan | H01L 33/44 257/13 |
| 2016/0005918 | A1 * | 1/2016 | Nataf | H01L 21/0254 257/13 |
| 2016/0043272 | A1 * | 2/2016 | Damilano | H01L 33/0075 257/13 |
| 2016/0087142 | A1 * | 3/2016 | Meyer | H01S 5/1096 315/246 |

OTHER PUBLICATIONS

S. Jung, S. Suchalkin, G. Kipshidze, D. Westerfeld, E. Golden, D. Snyder and G. Belenky, "Dual wavelength GaSb based type I quantum well mid-infrared light emitting diodes", Applied Physics Letters 96 (19) (2010).

S.Jung, S.Suchalkin, G.Kipshidze, D.Westerteld, G.Belenky, "Light-Emitting Diodes Operating at 2 With 10 mW Optical Power", Photonic Technology Letters, v.25 (23), pp. 2278-2280 (2013).

R.Q.Yang, Y. Qiu, "Bipolar cascade lasers with quantum well tunnel junctions", Journal of Applied Physics, v.94(11), pp. 7370-7372(2003).

* cited by examiner

Bulk active region

Quantum well active region

Superlattice active region

BI-DIRECTIONAL DUAL-COLOR LIGHT EMITTING DEVICE AND SYSTEMS FOR USE THEREOF

CROSS-REFERENCE TO RELATED APPLICATION

This application claims the benefit of Provisional Patent Application Ser. No. 62/020,580, filed on Jul. 3, 2014 by present inventors.

FEDERALLY SPONSORED RESEARCH

This work was funded by the United States Air Force under contract FA8651-12-C-0079

SEQUENCE LISTING OR PROGRAM

Not Applicable

FIELD OF THE DISCLOSURE

The present invention is related to semiconductor electro-optical device design. More particularly, present invention teaches a structure of a light emitting semiconductor device that can be used as a source of electromagnetic radiation of two different wavelengths, suitable for implementation of highly efficient, low-cost gas detection system.

BACKGROUND OF THE INVENTION

Gas sensors have applications spanning much of the human experience. Research, industrial, safety, consumer, medical, and military applications abound. Many of gases of interest have absorption spectral features in the mid infrared that can be used to detect and differentiate between these gases. The combination of atmospheric transparency, strong spectral signatures, and availability of efficient light sources and detectors makes the mid-infrared (mid-IR) an attractive wavelength region for gas spectroscopy. For the purpose of the present disclosure, the discussion below is referring to gases, while it would be easily discovered by a skilled artisan that all principles disclosed below can be equally applied to the detection of liquids and gels; the materials that can be all together characterized as non-solid substances.

A great many gas absorption spectroscopy systems have been developed. ["Differential absorption spectroscopy", U. Platt, J. Stutz, Springer Verlag Berlin Heidelberg, 2008] Systems that measure the complete mid-IR absorption spectrum provide the most information, but they can be expensive, power hungry, and physically large. Although these systems can detect multiple gases, they are poorly suited for many gas detection applications, such as leaks detection, environment monitoring etc. where cost, power consumption, and size are paramount factors.

Alternatively, systems can be designed to use only two wavelengths: an absorption wavelength that is absorbed by the gas under investigation, and a reference wavelength that is not. A comparison of the intensity of the absorption and reference wavelengths reveals the presence and concentration of the target gas. For many applications, an additional requirement is that neither wavelength should be absorbed by standard atmospheric gases. This permits the detection of target gas(es) diluted in the atmosphere.

There are many ways to generate the absorption and reference wavelengths. One is to use a single broadband light source, such as a glow bar, and wavelength selective filters. The selective filters of each of the above wavelengths are altered using mechanical actuator system (for example, a rotating disc with holes where the filters are physically mounted). This approach is attractive in that the probe and reference wavelengths originate from the same physical space, and any variations in the input optical power can be expected to affect both absorption and reference wavelengths in a similar way. It is unattractive in that most of the broadband optical power is wasted and that only low frequency variations in the source intensity can be compensated for due to the slow mechanically actuated filter system.

Another option improves power efficiency by utilizing two independent and relatively narrow spectrum light sources. If the narrow light sources are Light Emitting Diodes (LEDs), then they can be alternated rapidly using a pseudorandom sequence. A correlation analysis of the detector signal with the pseudorandom sequence greatly reduces noise in this approach. Power efficiency is also improved due to the efficiency of LEDs compared to broadband sources and the fact that only useful wavelengths are generated.

The Gallium Antimonide (GaSb) material system can produce LEDs covering the spectral range of the infrared (IR) light with the wavelength from 2 to 12 um, permitting the detection of many gases, including methane, a commercially and environmentally important gas.

The approach of using two narrow band light sources, such as LEDs, has some downsides as well. In particular, the optical complexity of the system increases, the light of the two wavelengths does not share the same optical path, and the sources operate at independent, possibly different temperatures. The increased optical complexity adversely impacts the cost and the size of the detector, and as a result of the entire system. Any variations in the optical alignment due to mechanical vibrations or thermal imbalance may produce measurement and detection errors. While these errors can be theoretically "averaged away" using correlation analysis, the result could be slower measurements and increased power consumption.

The independence and possible differing of the temperatures of the two light sources is a more fundamental problem. The efficiency and central emission wavelength of all existing LEDs is dependent on temperature; these effects are particularly evident for mid-IR LEDs since they use narrow band gap semiconductor materials whose properties are very sensitive to temperature. Further, the temperature of the LED is affected by self-heating from its own bias current. A pseudorandom variation in LED current results in a correlated pseudorandom variation in the wavelength of the emitted light and its intensity. A correlation analysis is then not effective in countering this subtle problem.

In the light of the above, the best possibility for an LED-based gas detection system would be to use a single narrow-band light source along with a single wideband detector. This design has many advantages, a simplified optical arrangement being the most evident. However, in order to achieve such system, that single narrow-band light source must emit two different wavelengths of light from the same physical space. LEDs can do this by means of extreme temperature shifts, but achieving these temperature shifts is slow and introduces errors due to the varying temperature of the LED. Pseudorandom correlation becomes impractical at the low speeds achievable with temperature based wavelength tuning.

There is a need, therefore, for a light source that would produce a dual color, narrow band light emission from the same physical space, with independent or correlated control of the light intensity of each color. It is further desired that the said dual color light source is simple, low cost and easy in both mounting and control. Each wavelength, or a "color", of a dual light color source should respectively correspond to an absorption and transmission spectra of a gas targeted for detection in a certain gas detection system.

The present invention teaches the design of such dual color LED that emits the light of one of the two pre-selected wavelengths in the IR region of the spectra, depending on the polarity of the applied external electric bias. These and other advantages of the present invention will be more readily understood from the following discussion taken in conjunction with the accompanying drawings.

Figure 6:
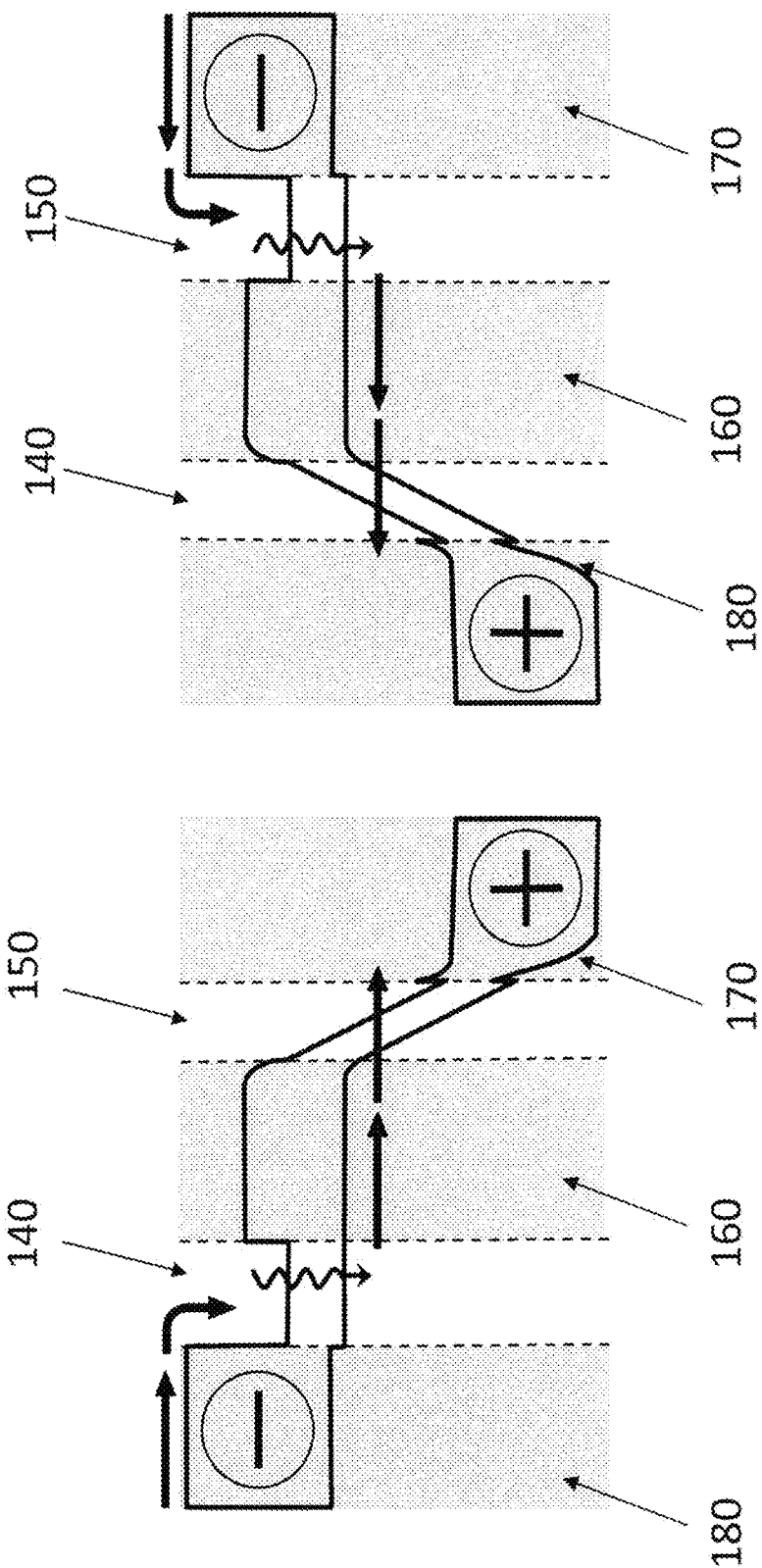

A schematic band diagrams of the n-p-n embodiment of the dual color LED of present invention under different polarities of the external electric bias are presented in FIG. 6.

Figure 7:
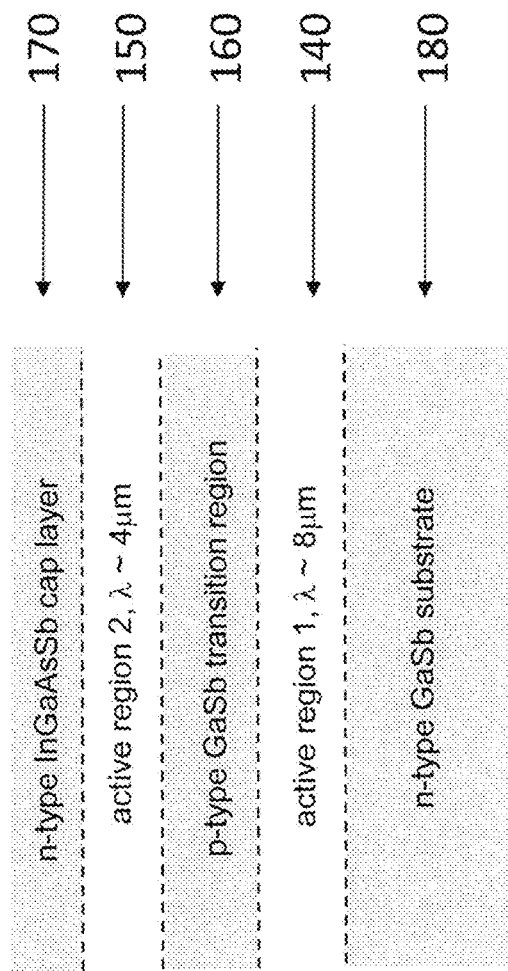

FIG. 7 schematically represents the epitaxial layer structure of the example dual color LED device as per the teachings of the present invention.

Figure 8:
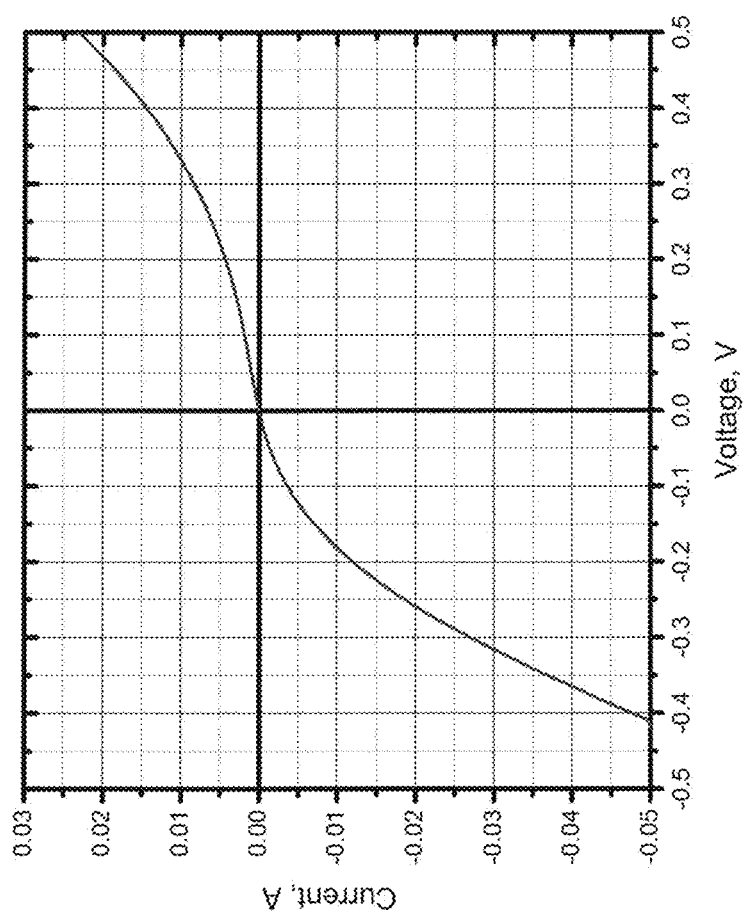

FIG. 8 provides the current-voltage characteristic of the example dual color LED device as per the teachings of the present invention.

Figure 9:
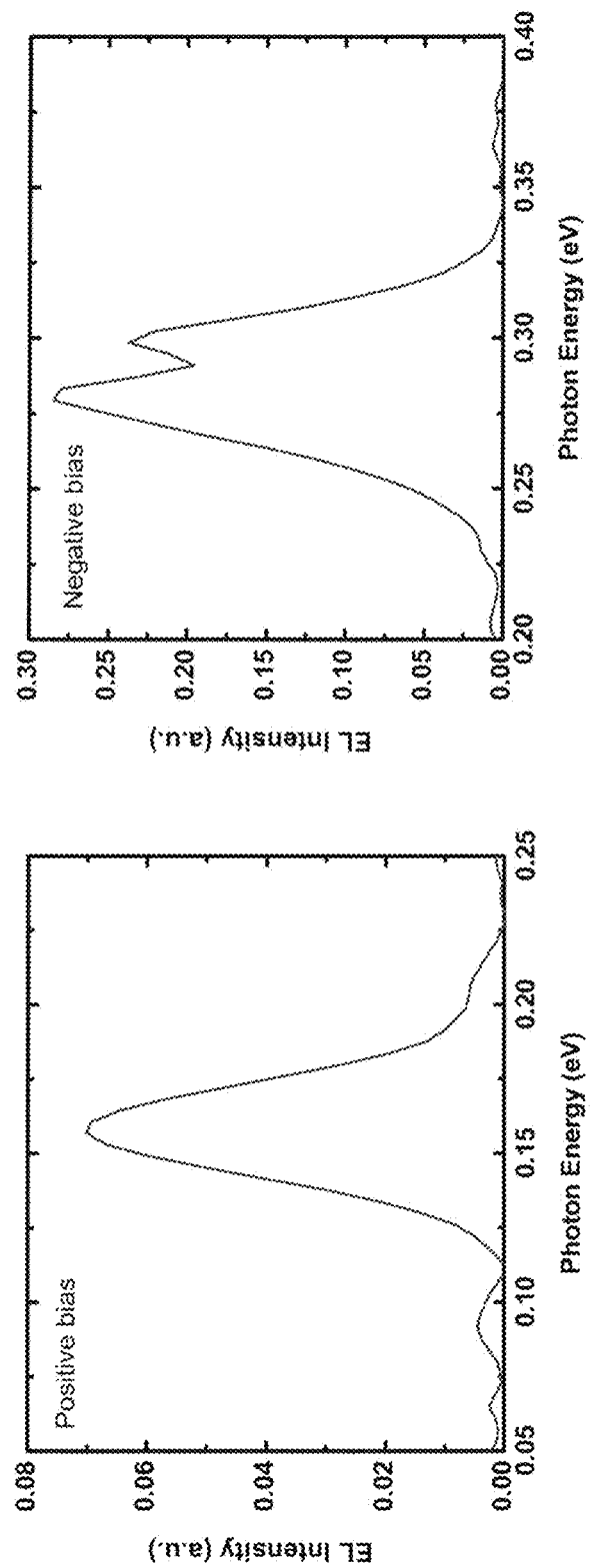

FIG. 9 provides the emission spectra characteristics of the example dual color LED device as per the teachings of the present invention at different bias polarities.

PRIOR ART BY THE SAME INVENTORS

Figure 1:
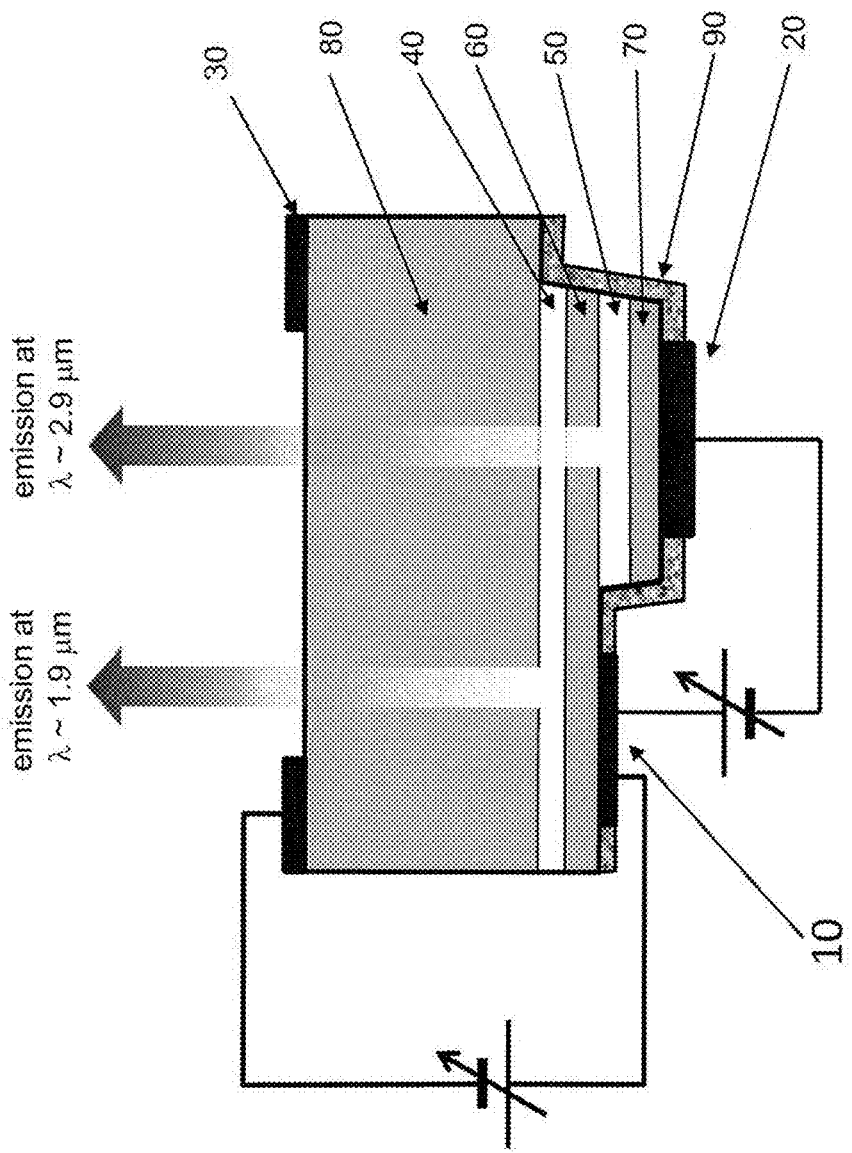
FIG. 1 represents the prior art dual color, three-electrode LED schematic layer structure and terminal layout.

Dual color LEDs have been demonstrated by the same group of inventors in the past for the infrared scene projection applications [S. Jung, S. Suchalkin, G. Kipshidze, D. Westerfeld, E. Golden, D. Snyder and G. Belenky, Applied Physics Letters 96 (19) (2010).] The schematic layout of the prior art device is presented in FIG. 1. In order to establish independent control of the intensities of the two wavelengths, three terminals were required: a common anode 10 and two independent cathodes 20 and 30. While these three terminals permit independent control of the two wavelengths, the third terminal greatly complicates fabrication, increases cost, and reduces yield.

A three-electrode LED, or, more precisely, Light Emitting Triode (LET) had an active region comprising two parts 40 and 50, separated by an injection layer 60. Each part 40 and 50 contained an active area with efficient direct radiative electron-hole recombination, emitting the light of different wavelength (1.9 um for active region part 40 and 2.9 um for active region part 50) within a single device. The intensity ratio between two colors was controlled by two voltages: between the cap layer 70 and injection layer 60 (color 1) and between injection layer 60 and the substrate 80 (color 2). The surface isolation between a common anode 10 and the one of the independent cathodes 20 contacting the cap layer 70 was achieved using passivation dielectric layer 90.

In order to perform its function, an LET comprised three electrical terminals 10, 20 and 30 providing the contacts, respectively, to the injection layer 60, cap layer 70 and substrate 80. The first two contacts 10 and 20 were positioned on the epi-layer side of the structure, in order to provide efficient light emission from the substrate 80 side of the structure. Accordingly, these two contacts 10 and 20 were positioned at laterally different areas. Since the electric current spreading in the LED epilayers was not effective, especially at high currents, the emitting areas of the light of colors 1 and 2 also had different lateral shape.

In the optical gas sensor system, the emission area of the LED is imaged onto the detector. If an LET from this example was used in such a system, different emitting areas for the absorption and reference wavelengths would lead to additional complications, as they would be imaged to different regions on the detector surface.

SUMMARY OF THE INVENTION

Provided is an LED optimized for use in low-cost gas detection systems, the LED emitting two wavelengths ("colors") of infrared light from the same aperture. The dual color LED is useful in gas detection since one device emits a wavelength centered on an absorption line and also emits a reference wavelength that is not absorbed by a target gas, while both wavelengths are transmitted through the atmosphere with low loss. The presence of target detection gas is determined by comparing the intensities of the absorption and reference wavelengths after the light has traversed a sample.

The LED device simplifies and reduces the cost of absorption based gas detectors. Since the absorption and reference wavelengths are emitted from the same exact aperture, both wavelengths can share the same optical path, reducing the size and cost of the detector while also reducing potential sources of error due to optical path variation.

The high modulation speed of the LED of the present invention permits switching between the colors rapidly in a pseudorandom sequence so that correlation analysis can significantly reduce error without increasing cost.

DETAILED DESCRIPTION OF THE INVENTION

Figure 2:
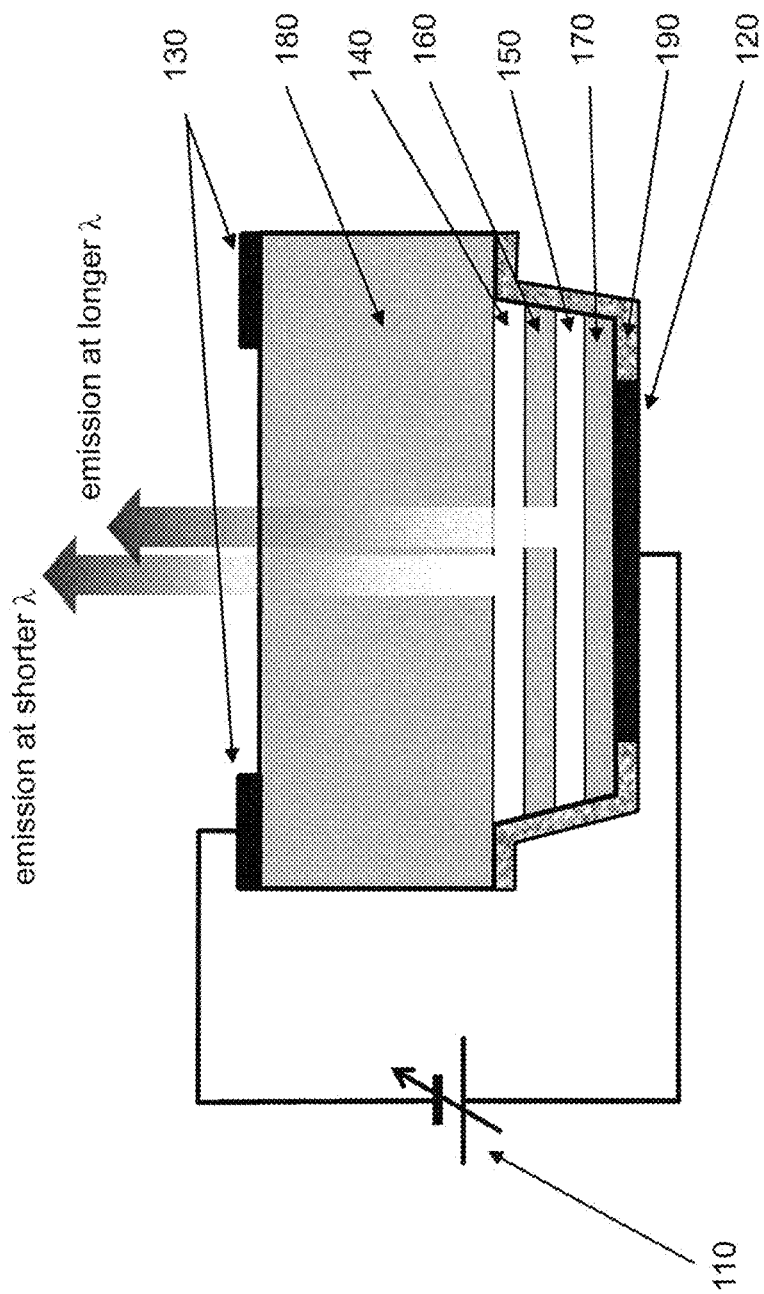
FIG. 2 represents the schematic layer structure and terminal layout of the dual color LED of present invention.

The schematic layout of the dual-color LED optimized for a gas detection system is depicted in FIG. 2. The layout comprises a substrate 180 of a first carrier type (p-type or n-type), an epitaxially grown transition layer 160 of a second carrier type (n-type or p-type, respectively), and an epitaxially grown cap layer 170 of the first carrier type. A first epitaxially grown active region 140 emitting a light of a first wavelength is sandwiched between the substrate 180 and the transition layer 160. A second epitaxially grown active region 150 emitting a light of a second wavelength is sandwiched between the cap layer 170 and the transition layer 160. It is noted that the first wavelength is shorter than the second wavelength, in order to avoid absorption of the light of the second wavelength by the first active region 140. A metal contact 120 is deposited on top of the cap layer 170, and another metal contact 130 shown in the picture as two disconnected portions, but optionally connected outside of the picture plane is deposited on the back side of the substrate 180. The back side of the substrate is defined as a side opposite to the side on which epitaxial growth of the semiconductor layers is performed. An external bi-directional power source 110 can be further connected to contacts 120 and 130 to achieve the light emission from the device.

Figure 3A:
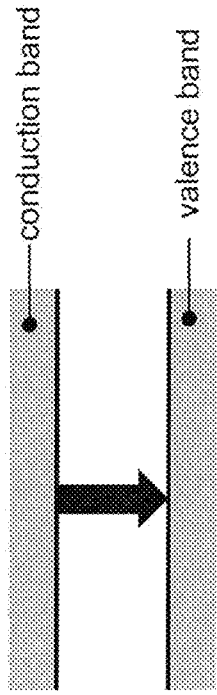
FIGS. 3A-3C demonstrate three possible designs of the active regions of the dual color LED of the present invention.
Figure 3B:
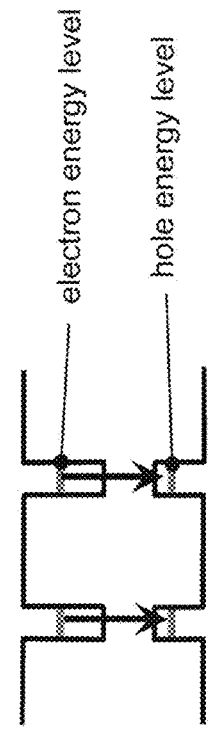
Figure 3C:
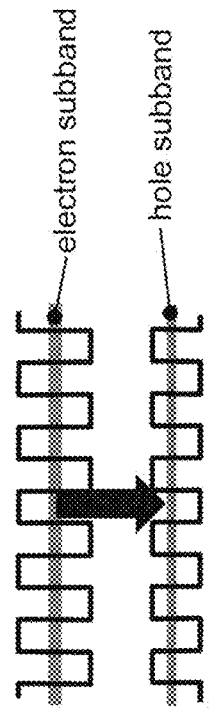

The exact detailed structures of the active regions 140 and 150 are not essential for the present invention and could be discovered by an artisan skilled in the art. The three most conventional band diagrams corresponding to the possible active regions structures are shown in FIG. 3. FIG. 3a demonstrates the schematic band diagram (without external electric bias) of a bulk active region comprising a single semiconductor material. FIG. 3b demonstrates the schematic band diagram (without external electric bias) of a quantum well active region comprising a semiconductor material of a first band gap with inclusion(s) of a second semiconductor material of a second band gap, where the second band gap is narrower than the first band gap, the inclusion(s) of the second material having thickness(es) small enough to create (a) quantum well(s) for carrier localization. FIG. 3c demonstrates the schematic band diagram (without external electric bias) of a superlattice active region, which is similar to the quantum well active regions where the inclusions of the narrow band semiconductor materials are separated by short distances, which allows for a sub-band creation that is common for multiple quantum wells. The black arrows in FIG. 3 illustrate the optical transition (radiative electron-hole recombination process).

Figure 4:
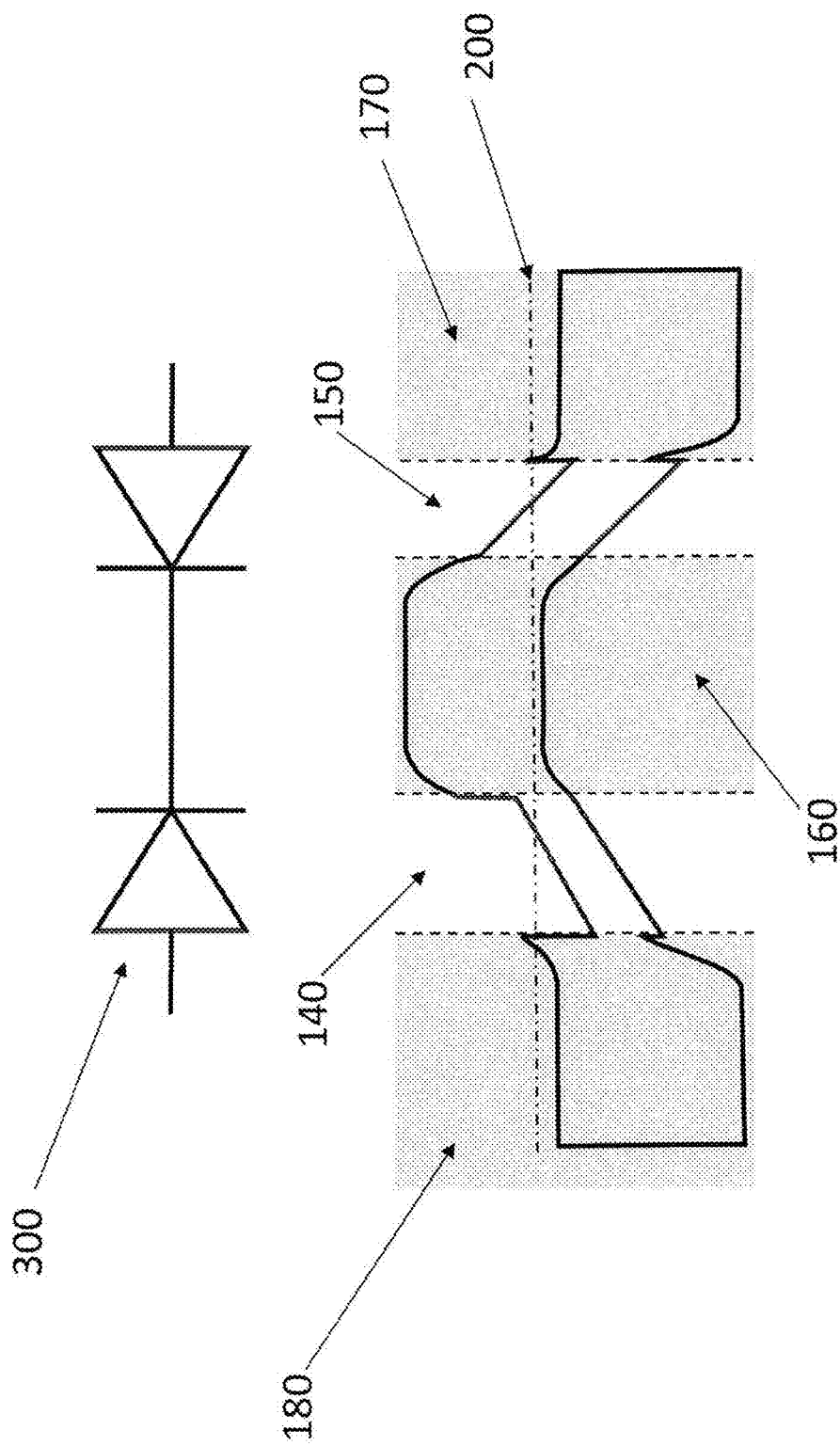
FIG. 4 depicts schematic band diagram of the n-p-n embodiment of the dual color LED of present invention in the absence of the external electric bias, and an equivalent circuit representation of the same.

A schematic band diagram (without external bias) of the dual-color LED of one of the embodiments of the present invention is shown in FIG. 4. The embodiment comprises the substrate 180 of n-type, the transition layer 160 of p-type, and the cap layer 170 of n-type. For simplicity, the first and the second active regions 140 and 150 with bulk structure of FIG. 3a are shown. Note that due to typical difference in the effective masses of electrons and holes, the Fermi energy 200 of the structure lays slightly higher than the valence band edge in p-material of the transitional layer 160, and also slightly above the conduction band edge in n-materials of the substrate 180 and the cap layer 170. A circuit schematic representation 300 of the structure is also shown.

A key aspect of the dual-color LED of this n-p-n embodiment is the design of the p-type transitional layer 160. The top of the valence band of the active regions 140 and 150 and the transitional layer 160 are aligned in order to facilitate the hole transport. As a result, the core operating principle of the device is realized: that each active region emits light under forward bias, and conducts current easily when reverse biased without emitting light.

Figure 5:
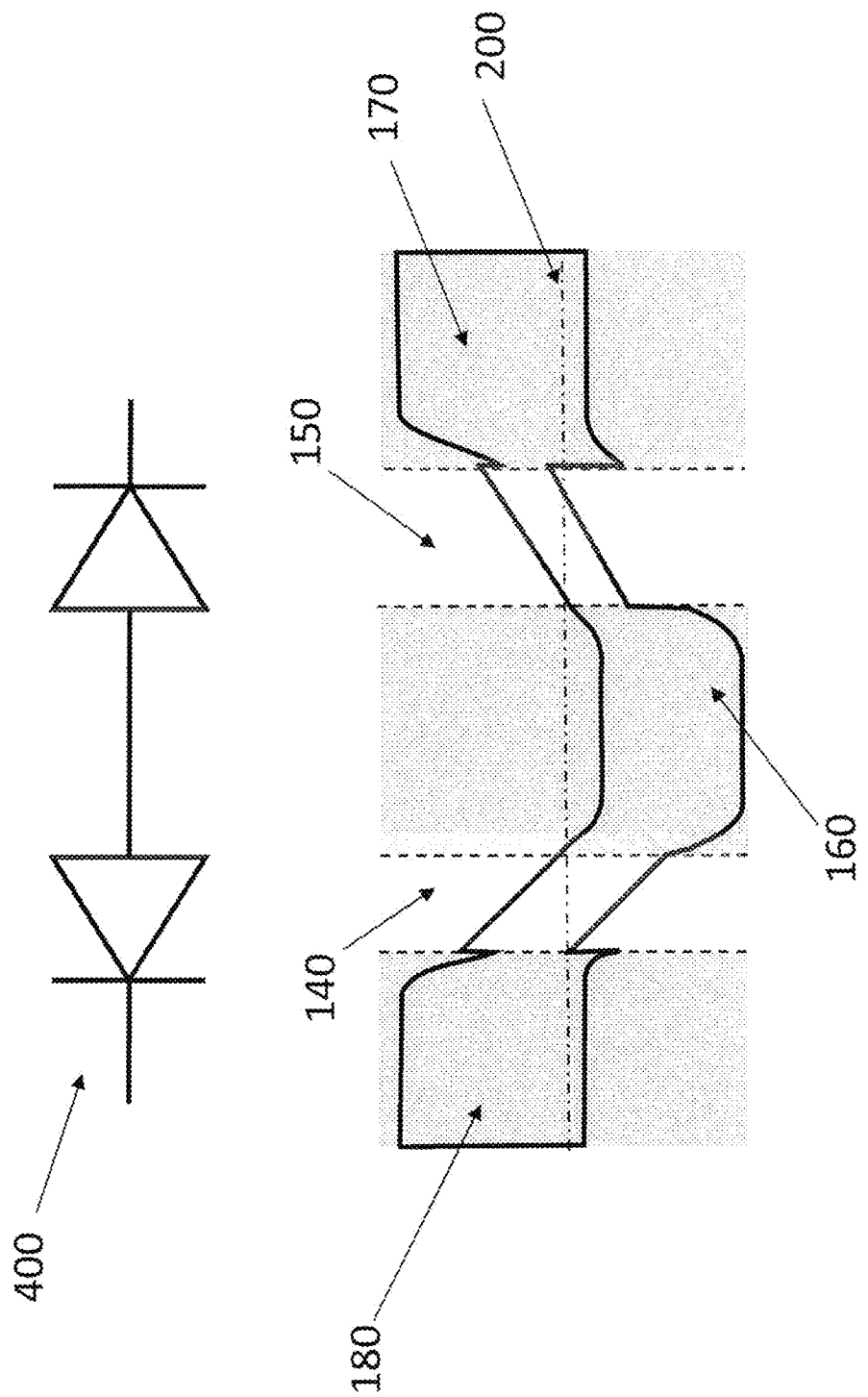
FIG. 5 depicts schematic band diagram of the p-n-p embodiment of the dual color LED of present invention in the absence of the external electric bias, and an equivalent circuit representation of the same.

A schematic band diagram (without external bias) of the dual-color LED of one of the embodiments of the present invention is shown in FIG. 5. The embodiment comprises the substrate 180 of p-type, the transition layer 160 of n-type, and the cap layer 170 of p-type. For simplicity, the first and the second active regions 140 and 160 with bulk structure of FIG. 3a are shown. Note that due to typical difference in the effective masses of electrons and holes, the Fermi energy 200 of the structure lays slightly higher than the conduction band edge in n-material of the transitional layer 160, and also slightly above the valence band edge in p-materials of the substrate 180 and the cap layer 170. A circuit schematic representation 400 of the structure is also shown.

A key aspect of the dual-color LED of this p-n-p embodiment of FIG. 5 is the design of the n-type transitional layer 160. The bottom of the conduction band of the active regions 140 and 150 and the transitional layer 160 are aligned in order to facilitate the electron transport. As a result, the core operating principle of the device is realized: that each active region emits light under forward bias, and conducts current easily when reverse biased.

FIG. 6 illustrates this core operating principle in case of the p-n-p embodiment of FIG. 4. This embodiment is selected for illustration without limiting the scope of the present invention; a skilled artisan can apply the illustrated principle to the n-p-n embodiment without any difficulty. In FIG. 6, two schematic band diagrams of FIG. 4 are shown under different bias polarities. The polarities are depicted by symbols "+" and "−" in circles. Here again, the simplest case of bulk active regions are shown without limiting the scope of the invention. When positive bias is applied to the cap layer 170 with respect to the substrate 180, the first active region 140 is forward biased and produces the light, while the second active region 150 is reverse biased and conducts current due to the hole tunneling from the valence band of the transitional layer 160 into the conduction band of the cap layer 170 under high electric field. Respectively, when negative bias is applied to the cap layer 170 with respect to the substrate 180, the second active region 150 is forward biased and produces the light, while the first active region 140 is reverse biased and conducts current due to the hole tunneling from the valence band of the transitional layer 160 into the conduction band of the substrate 180 under high electric field.

Example Structure

In order to validate the teachings of the present invention, a dual-color LED optimized for the gas detection system was fabricated using GaSb material system. The layout structure of this example device is presented in FIG. 7. The bulk substrate 180 of n-type GaSb material was obtained from a commercial vendor. A first active region 140 emitting the light of the wavelength of ~8 um (photon energy ~0.15 eV) was grown using Molecular Beam Epitaxy (MBE). Next, the transitional layer 160 comprising a p-type GaSb material was grown by MBE on top of the first active region 140. After that, the second active region 150 emitting the light of the wavelength of ~4 um (photon energy ~0.3 eV) was grown by MBE on top of the transitional layer 160, followed by the cap layer 170 comprising n-type $In_{0.1}GaAs_{0.088}Sb$ composition growth by MBE.

Fabrication of this exemplary dual-color LED included a deep etched 400 um wide round mesa with top annular contact deposited onto the substrate. The device was mounted epi-layer side down; the emission was out-coupled through the substrate surface.

As illustrated above, when conducting the electric current, one active region of the device is under forward bias and emits light, while the other is under reverse bias and conducts without emitting light. The question in this approach is whether a reverse-biased p-n junction can transmit high current without permanent damage. Reverse biased diodes have been successfully used as a connection region in type I cascaded lasers and LEDs [S. Jung, S. Suchalkin, G. Kipshidze, D. Westerfeld, G. Belenky, Photonic Technology Letters, v. 25 (23), pp. 2278-2280 (2013), R. Q. Yang, Y. Qiu, Journal of Applied Physics, v. 94(11), pp. 7370-7372 (2003)]. More than 10 milliwatts of the optical power at room temperature was obtained from a two-cascade LED where the current was injected into second cascade through the reverse biased GaSb p-n junction. The bias voltage for this two-cascade device was increased by a factor of ~2 which indicates low voltage loss across the reverse biased unction between the cascades. No damage was observed. As long as the bandgap of the active regions materials of the dual-color LED of the present invention is less than the bandgap of GaSb, low voltage losses are expected on the reverse biased heterostructure.

The I-V characteristic of the fabricated exemplary dual-color LED is presented in FIG. 8. Here, positive voltage corresponds to the higher potential of the substrate. As expected above, there is no voltage blocking by a reverse-biased p-n junction in any direction of the current.

The emission spectra of the fabricated exemplary dual-color LED is presented in FIG. 9. When positive bias is applied to the substrate, the device emits light that peaks at the photon energy around 0.15 eV. When negative bias is applied to the substrate, the device emits light that peaks at the photon energy around 0.28 eV.

Thus, the example validates that the present invention enables the two-terminal, dual-color LED emitting the light of two different wavelengths in the IR region of the spectra, depending on the polarity of the allied electric signal, from the same physical aperture. Such a device is optimized for usage in the low-cost, simple and yet reliable gas detection systems that can find wide range of applications, including household natural gas/methane/carbon monoxide detection systems and pipeline monitoring systems.

What is claimed is:

1. A two-terminal light emitting semiconductor device comprising:
    a) A first and a second active regions having radiative recombination as dominant carrier recombination mechanism;
    b) a first carrier supply region of a first carrier type sandwiched between the first and the second active regions;
    c) a second carrier supply region of a second carrier type adjacent to the first active region in such a way that said first active region is sandwiched between the first carrier supply region and the second carrier supply region, the second carrier supply region connected to a first of the two semiconductor device terminals;
    d) a third carrier supply region of the second carrier type adjacent to the second active region in such a way that said second active region is sandwiched between the first carrier supply region and the third carrier supply region, the third carrier supply region connected to a second of the two semiconductor device terminals;
wherein said two-terminal light emitting semiconductor device produces a first wavelength of light when biased with a first sign of a polarity of an electric bias, and produces a second wavelength of light when biased with a second sign of the polarity of the electric bias applied to the terminals of said light emitting semiconductor device wherein the second sign is opposite the first sign.

2. A semiconductor device of claim 1 where at least one of said active regions comprises a bulk material having radiative recombination as dominant carrier recombination mechanism.

3. A semiconductor device of claim 1 where at least one of said active regions comprises a structure with localized quantum state of the carrier, the structure selected from the group of quantum well and superlattice.

4. A semiconductor device of the claim 3 where each of said active regions conducts similar current densities in both forward and reverse directions with respect to the polarity of adjacent carrier supply regions, emits light when biased in forward direction with respect to the polarity of adjacent carrier supply regions, and non-radiatively conducts electric current when biased in reverse direction with respect to the polarity of adjacent carrier supply regions.

5. A semiconductor device of the claim 4 where the first carrier supply region is p-type and does not have an external electrical connection attached to it, and the second and the third carrier supply regions are n-type and have external electrical connections attached to them.

6. A semiconductor device of the claim 5, with said active regions producing the light of the wavelength in the infrared region of the spectra, when biased in forward direction with respect to the polarity of adjacent carrier supply regions.

7. A semiconductor device of the claim 6 where the wavelength of the light produced by both said active regions belongs to an atmospheric transparency window.

8. A semiconductor device of the claim 7 where the wavelength of the light produced by one of the active regions belongs to a transparency window of a pre-selected non-solid substance, whereas the light produced by the other of the active regions belongs to the absorption window of that said pre-selected non-solid substance.

9. A non-solid substance detection system comprising the semiconductor device of claim 8, detecting the presence of the non-solid substance that is transparent to a wavelength of the light emitted by one of said active regions, and is not transparent to a wavelength of the light emitted by another of said active regions.

10. A semiconductor device of the claim 4 where the first carrier supply region is n-type and does not have an external electrical connection attached to it, and the second and the third carrier supply regions are p-type and have external electrical connections attached to them.

11. A semiconductor device of the claim 10, with said active regions producing the light of the wavelength in the infrared region of the spectra, when biased in forward direction with respect to the polarity of adjacent carrier supply regions.

12. A semiconductor device of claim 11 where the wavelength of the light produced by both said active regions belongs to an atmospheric transparency window.

13. A semiconductor device of claim 12 where the wavelength of the light produced by one of the active regions belongs to a transparency window of a pre-selected non-solid substance, whereas the light produced by the other of the said active regions belongs to the absorption window of that said pre-selected non-solid substance.

14. A non-solid substance detection system comprising the semiconductor device of claim 13, detecting the presence of the non-solid substance that is transparent to a wavelength of the light emitted by one of said active regions, and is not transparent to a wavelength of the light emitted by another of said active regions.

* * * * *